(12) United States Patent
Langone

(10) Patent No.: US 7,597,196 B2
(45) Date of Patent: Oct. 6, 2009

(54) INSULATED MEDICATION CARRYING CASE

(76) Inventor: Phyllis Langone, 533 N. 7th St., New Hyde Park, NY (US) 11040

( * ) Notice: Subject to any disclaimer, the term of this patent is extended or adjusted under 35 U.S.C. 154(b) by 0 days.

(21) Appl. No.: 11/759,837

(22) Filed: Jun. 7, 2007

(65) Prior Publication Data

US 2007/0284278 A1    Dec. 13, 2007

Related U.S. Application Data

(60) Provisional application No. 60/811,963, filed on Jun. 8, 2006.

(51) Int. Cl.
*A61B 19/02* (2006.01)
*F25D 3/08* (2006.01)
(52) U.S. Cl. .................. 206/438; 62/371; 62/457.9; 206/364
(58) Field of Classification Search ......... 206/364–365, 206/438, 528–540, 570–572; 62/371, 457.1–457.9
See application file for complete search history.

(56) References Cited

U.S. PATENT DOCUMENTS

| | | | | |
|---|---|---|---|---|
| 4,573,581 A | * | 3/1986 | Galloway et al. | 206/570 |
| 4,738,364 A | * | 4/1988 | Yeager | 62/457.1 |
| 4,955,480 A | * | 9/1990 | Sexton | 206/438 |
| 5,078,267 A | * | 1/1992 | Wright | 206/364 |
| 5,390,791 A | * | 2/1995 | Yeager | 206/438 |
| 5,806,670 A | * | 9/1998 | Harlan et al. | 206/538 |
| 5,865,032 A | * | 2/1999 | MacPherson et al. | 62/457.9 |
| 5,956,968 A | * | 9/1999 | Grabowski | 62/457.2 |
| 6,595,362 B2 | * | 7/2003 | Penney et al. | 206/364 |
| 6,935,133 B2 | * | 8/2005 | Keeter et al. | 62/371 |

FOREIGN PATENT DOCUMENTS

EP    397607 A1 * 11/1990

* cited by examiner

*Primary Examiner*—Byron P Gehman
(74) *Attorney, Agent, or Firm*—West and Associates, APC; Stuart J. West; Charlotte Rodeen-Dickert

(57) ABSTRACT

A portable device for transporting or storing pharmaceuticals under refrigeration. The pharmaceuticals can be in a medication container or medical device, such as a syringe. A user chills the entire device or a cooling component within the device, and then places the pharmaceutical item inside the device and closes the device around it. The pharmaceutical device may then be transported while being kept at a reduced temperature by the device.

7 Claims, 4 Drawing Sheets

INSULATED MEDICATION CARRYING CASE

STATEMENT OF PRIORITY

The following application claims priority to U.S. Provisional Patent Application No. 60/811963, filed Jun. 8, 2006, the complete contents of which are hereby incorporated by reference.

BACKGROUND

1. Field of the Invention

The present disclosure relates to the field of storage and transport of medical devices and medication.

2. Background

Many types of medication must be kept at a proper temperature to prevent spoilage or loss of efficacy of the drug. This often involves keeping a medication refrigerated at a particular temperature. In a clinical setting with a refrigerator, this is not a difficult task. However, if the medication must be transported or a patient wishes to carry it with him, keeping it at the proper temperature for an extended length of time can present a challenge.

For example millions of diabetics require an insulin injection prior to every meal. However, the insulin must be kept refrigerated prior to use. This does not present much difficulty if the person is at home, since the insulin may simply be stored in a refrigerator. If the person is away from home, though, he must either have refrigerated insulin at the destination, or, more likely, transport it with him.

In order to keep the insulin refrigerated during transport, one could pack a syringe into a plastic bag and then surround it with ice or a freezer cold pack. However, this is cumbersome and inconvenient. The person must carry around a bulky and awkward package in a purse, totebag, or briefcase. Further, ice can leak all over a person's bag, while a cold pack does not stay cold for very long.

What is needed is a convenient and portable device to refrigerate medications. A pocket or purse-sized insulated case that could keep the medication refrigerated and ready to use would allow medication-dependent patients more freedom to go out and lead a more normal life.

DETAILED DESCRIPTION

Figure 1:
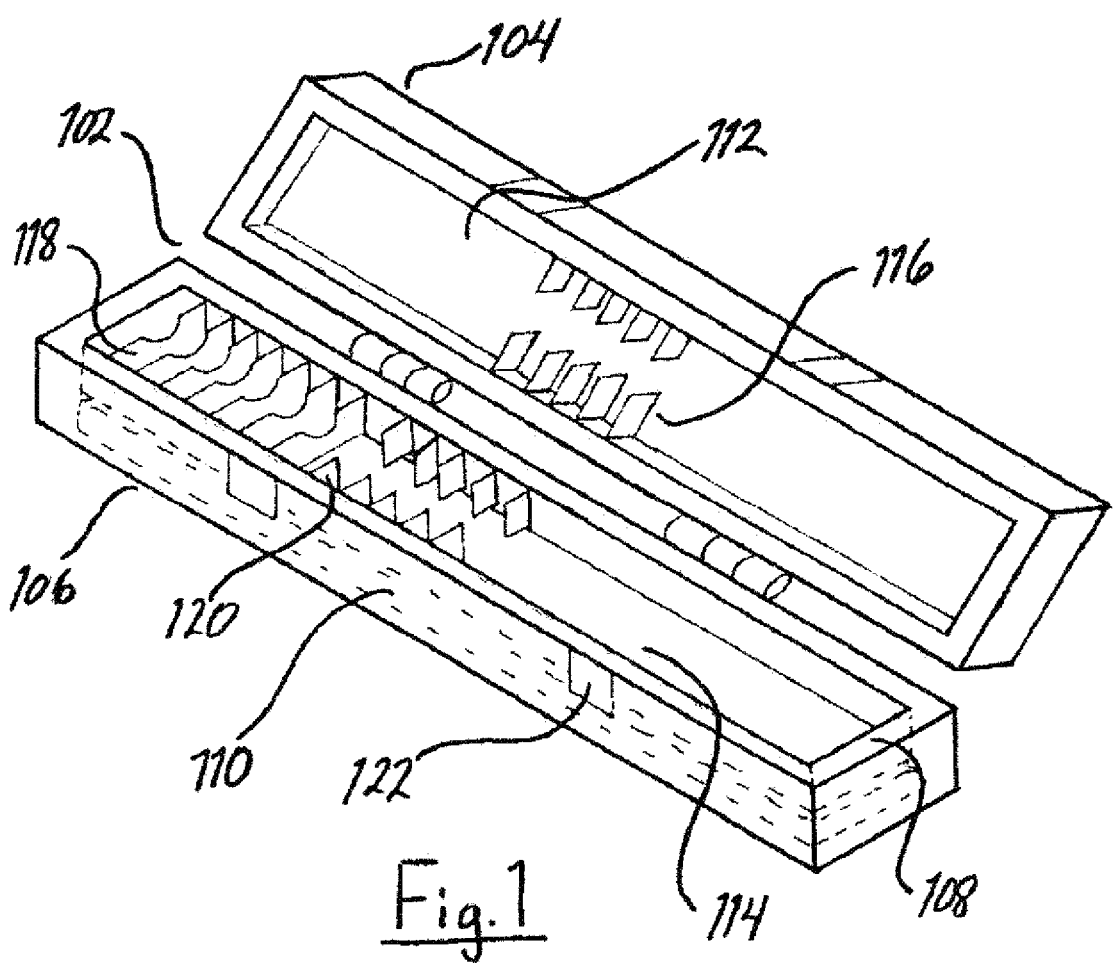
FIG. 1 depicts a perspective view of one embodiment of the present device.

FIG. 1 depicts a perspective view of one embodiment of the present device. An outer shell 102, having an interior surface and an exterior surface, can be separated substantially along its horizontal midline into an upper section 104 and a lower section 106. The upper section 104 and lower section 106 can be pivotally connected along adjoining longitudinal edges such that the upper section 104 and the lower section 106 can couple and uncouple with each other. A layer of insulating material 108 can line the interior of an outer shell 102. An upper section 104 and a lower section 106 can each house a cooling component 110. A first insert 112, having a proximal end and a distal end, can be removably coupled with the open edge of an upper section 104, thereby securing a cooling component 110 within an upper section 104. Said first insert 112 can be held in place by friction, adhesive, hook-and-loop closures, clips, or any other known/and or convenient mechanism. In the embodiment shown in FIG. 1, a lower section 106 can also house a cooling component 110. A second insert 114, having a proximal end and a distal end, can be removably coupled with the open edge of a lower section 106, thereby securing a cooling component 110 within a lower section 104. A second insert 114 can be held in place by friction, adhesive, hook-and-loop closures, clips, or any other known/and or convenient mechanism. At least one closure device 122 can be integrated with or affixed to the exterior of said outer shell 102.

Figure 1A:
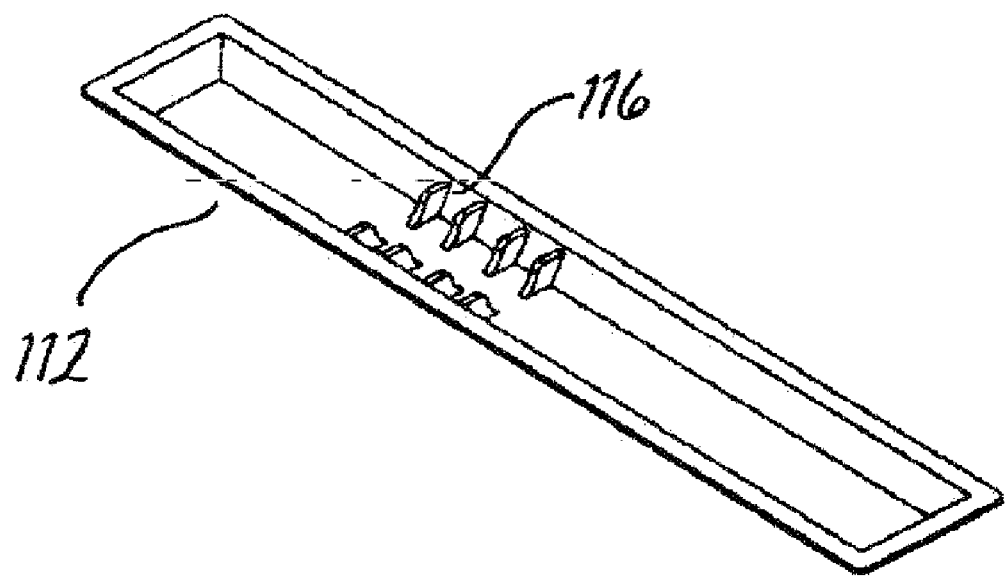
FIG. 1a depicts a perspective view detailing one embodiment of a component of the present device.

As shown in FIG. 1a, in some embodiments a first insert 112 can have a plurality of substantially parallel tabs 116 protruding in pairs from the interior longitudinal walls of a first insert 112. The pairs of tabs 116 can be grouped together, uniformly spaced, and located proximal to the transverse midline in the proximal half of a first insert 112.

Figure 1B:
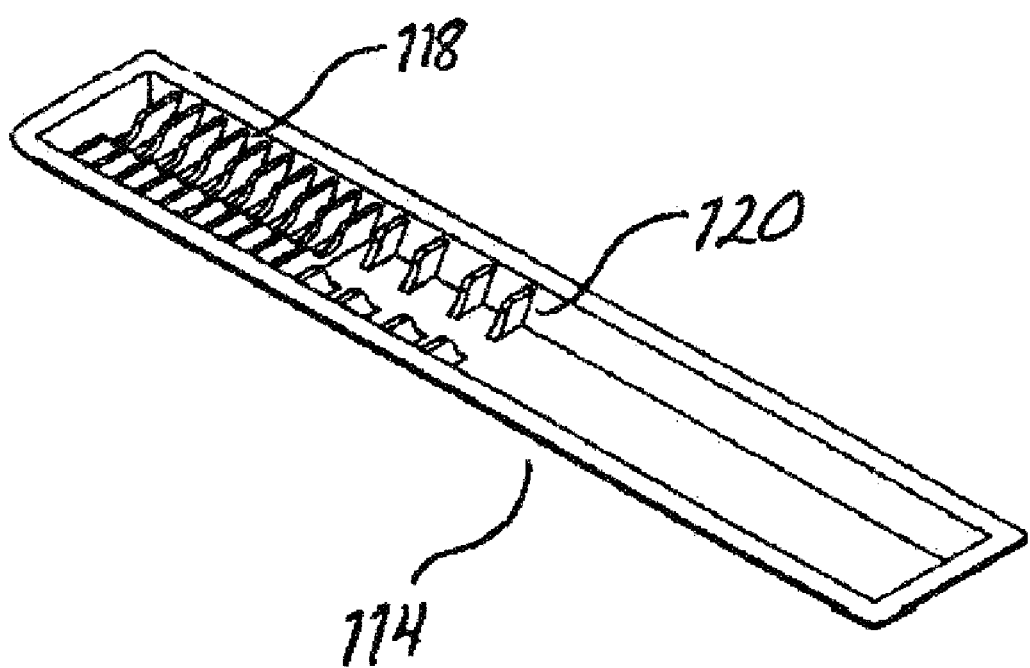
FIG. 1b depicts a perspective view detailing one embodiment of a component of the present device.

As shown in FIG. 1b, in some embodiments a second insert 114 can have a plurality of substantially parallel ridges 118 running substantially transversely between the interior longitudinal walls of a second insert 114. A plurality of ridges 118 can be grouped together, uniformly spaced, and located substantially near the proximal end of a second insert 114. A plurality of ridges 118 can each have a notch located substantially in the midline of the top edge of each ridge. A plurality of substantially parallel tabs 120 can protrude in pairs from the interior longitudinal walls of a second insert 114. A plurality of substantially parallel tabs 120 can be grouped together, uniformly spaced, and located adjacent to the distal end of a first plurality of substantially parallel ridges 118.

An outer shell 102 can be substantially rectangular, ovoid, or any other known and/or convenient geometry, and it can be made from plastic, nylon, or any other known and/or convenient material. In some embodiments, the material of an outer shell 102 can have insulating properties. In some embodiments, an outer shell can be further imprinted with text and/or images or feature a color that can indicate the contents of the device. In some embodiments, a layer of insulating material 108 can line the interior of an outer shell 102. This layer of insulating material 108 can be a metal, polymer, or any other known and/or convenient material.

A closure device 122 can be a latch, clip, magnetic coupling, or any other known and/or convenient mechanism for securing the upper section 104 and the lower section 106 of the outer shell 102 closed.

A cooling component 110 can be a chemical cold pack, gel, encased fluid, or any other known and/or convenient substance capable of remaining at cool temperatures for an extended period of time. A cooling component 110 can be integrated into, attached to, or freely set into a top section 104, a bottom section 106, or both sections.

A first insert 112 can be made from plastic, nylon, or any other known and/or convenient material. A plurality of substantially parallel tabs 116 can be integrated with, affixed to, or removably connected with the interior longitudinal walls and/or other interior surface of a first insert 112. In some embodiments a first insert 112 can be molded to include a plurality of substantially parallel tabs 116.

A second insert 114 can be made from plastic, nylon, or any other known and/or convenient material. A plurality of substantially parallel ridges 118 can be integrated with, affixed to, or removably connected with the interior longitudinal walls and/or other interior surface of a second insert 114. A plurality of pairs of substantially parallel tabs 120 can be integrated with, affixed to, or removably connected with the interior longitudinal walls and/or other interior surface of a second insert 114. In some embodiments a second insert 114 can be molded to include a plurality of substantially parallel ridges 118 and a plurality of pairs of substantially parallel tabs 120.

In other embodiments, said first insert 112 and said second insert 114 can have protrusions or recessed regions of a geometry corresponding to a specific type of medication container or device, such as, but not limited to, a bottle, syringe, "epipen," tube, or box.

In some embodiments, a user can place the entire device, containing or not containing the medication to be kept chilled, into a refrigerator, freezer, or any other known and/or convenient device to chill the device to the appropriate temperature.

In embodiments having at least one removable cooling component 110, a user can remove a cooling component 110 from the outer shell 102 and place them into a refrigerator, freezer, or any other known and/or convenient device to chill a cooling component to the appropriate temperature. When the user is ready to use the device to transport a container of medication, the user can place at least one cooling component 110 into either an upper section 104, a lower section 106, or both sections. If a user places a cooling component 110 into an upper section 104, a user can then removably couple a first insert 112 with the open edge of an upper section 104, thereby securing a cooling component 110 within an upper section 104. If a user places a cooling component 110 into a lower section 106, a user can then removably couple a second insert 114 with the open edge of a lower section 106, thereby securing a cooling component 110 within a lower section 106. The user then places a container of medication or a medical device containing medication inside the device, where it can be held in place by the protrusions of a first insert 112 and a second insert 114. The user can then close the outer shell 102 and secure it closed by a closure device 122.

Figure 2:
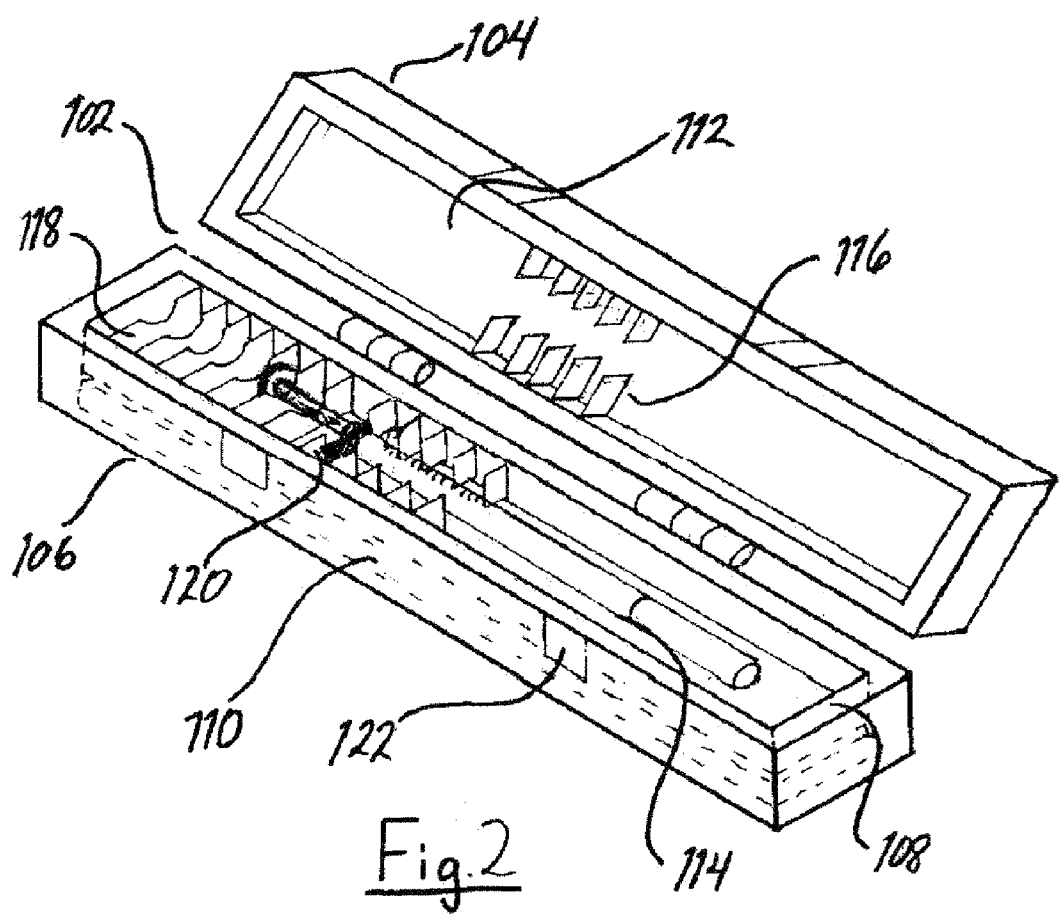
FIG. 2 depicts an embodiment of the present device in use.

In some embodiments, as shown in FIG. 2, a filled syringe can be placed such that the extended plunger shaft rests on one of the notches found on one of the substantially parallel ridges 118 running between the longitudinal walls of a second insert 114 and located substantially near the proximal end of a second insert 114. The end of the syringe plunger can then lie adjacent to the proximal side of one of the substantially parallel ridges 118. A syringe barrel can rest between one of the pairs of substantially parallel tabs 120, while the flat surfaces that extend perpendicularly from the proximal end of a syringe barrel can lie adjacent to the to the proximal side of one of the pairs of substantially parallel tabs 120. A syringe barrel can then rest substantially in the distal portion of a second insert 114.

When a user closes the device, one of pair of a plurality of substantially parallel tabs 116 can be positioned adjacent to the aforementioned flat surfaces on a syringe barrel to further secure a syringe in place within the device. A user can then secure the outer shell 102 closed by a closure device 122.

Although the invention has been described in conjunction with specific embodiments thereof, it is evident that many alternatives, modifications and variations will be apparent to those skilled in the art. Accordingly, the invention as described and hereinafter claimed is intended to embrace all such alternatives, modifications and variations that fall within the spirit and broad scope of the appended claims.

What is claimed is:

1. A device for storing and transporting medication, comprising:
    an outer shell, having an interior surface and an exterior surface, said shell being split substantially along its horizontal midline into a top section and a bottom section, each section having an open edge, wherein said top section and said bottom section are joined along a longitudinal edge such that said open edges of said sections open away from each other and close towards each other;
    at least one cooling component, wherein said sections house said at least one cooling component;
    at least one insert having at least one protrusion to restrict motion of a medication container placed within said device,
    wherein said at least one insert removably couples with an open edge of one of said sections to secure said at least one cooling component within said one section; and
    at least one closure mechanism.

2. The device of claim 1, further comprising a layer of insulating material adjacent to said interior surface of said outer shell.

3. The device of claim 1, wherein said at least one protrusion further comprises a plurality of paired and substantially parallel tabs.

4. The device of claim 1, wherein a second said insert has a proximal end and a distal end, an interior surface and an exterior surface, and having at least one protrusion to restrict motion of a medication container placed within said device.

5. The device of claim 4, wherein said at least one protrusion on said second insert further comprises a set of substantially parallel ridges, located at the proximal end of said second insert and each ridge extending completely transversely across the interior of said second insert, each ridge having a top edge and a notch cut substantially in the middle of said top edge;
    a set of pairs of substantially parallel tabs, located distal to said set of substantially parallel ridges, each pair of tabs extending towards each other transversely across said second insert.

6. The device of claim 5, wherein said outer shell further comprises distinguishing printing.

7. The device of claim 5, wherein said outer shell is of a distinguishing color.

* * * * *